(12) United States Patent
Hancock-Cooke

(10) Patent No.: US 7,727,217 B2
(45) Date of Patent: Jun. 1, 2010

(54) ABSORBENT ARTICLE WITH UNITARY ELASTOMERIC WAISTBAND WITH MULTIPLE EXTENSION ZONES

(75) Inventor: Catherine M. Hancock-Cooke, Neenah, WI (US)

(73) Assignee: Kimberly-Clark Worldwide, Inc, Neenah, WI (US)

( * ) Notice: Subject to any disclaimer, the term of this patent is extended or adjusted under 35 U.S.C. 154(b) by 1716 days.

(21) Appl. No.: 10/324,664

(22) Filed: Dec. 20, 2002

(65) Prior Publication Data

US 2004/0122411 A1 Jun. 24, 2004

(51) Int. Cl.
*A61F 13/15* (2006.01)
*A61F 13/20* (2006.01)

(52) U.S. Cl. ............. 604/394; 604/386; 604/389; 604/391; 604/393

(58) Field of Classification Search ............ 604/385.28, 604/385.29, 391–398
See application file for complete search history.

(56) References Cited

U.S. PATENT DOCUMENTS

| | | | |
|---|---|---|---|
| 4,205,679 A | 6/1980 | Repke et al. | |
| 4,515,595 A | 5/1985 | Kievit et al. | |
| 4,639,949 A | 2/1987 | Ales et al. | |
| 4,704,115 A * | 11/1987 | Buell .................... | 604/385.26 |
| 4,720,415 A | 1/1988 | Vander Wielen et al. | |
| 4,808,176 A | 2/1989 | Kielpikowski | |
| 4,857,067 A * | 8/1989 | Wood et al. .............. | 604/389 |
| 4,904,251 A | 2/1990 | Igaue et al. | |
| 4,936,840 A * | 6/1990 | Proxmire ............... | 604/385.22 |
| 5,242,436 A * | 9/1993 | Weil et al. .............. | 604/385.29 |
| 5,569,234 A | 10/1996 | Buell et al. | |
| 5,601,547 A | 2/1997 | Kato et al. | |
| 5,676,661 A | 10/1997 | Faulks et al. | |
| 5,683,376 A | 11/1997 | Kato et al. | |
| 5,711,832 A | 1/1998 | Glaug et al. | |

(Continued)

FOREIGN PATENT DOCUMENTS

EP 0803602 A1 10/1997

(Continued)

OTHER PUBLICATIONS

U.S. Appl. No. 09/563,417, filed May 3, 2000.

(Continued)

*Primary Examiner*—Melanie J Hand
(74) *Attorney, Agent, or Firm*—Dority & Manning, PA

(57) ABSTRACT

An absorbent article, such as a disposable diaper, includes a chassis having a front waist region, a back waist region, and a crotch region extending between the front and back waist regions. An outer cover member and a bodyside liner extend longitudinally between the front and back waist regions. An absorbent body structure is sandwiched between the outer cover member and the bodyside liner. A unitary elastomeric structure is attached to at least one of the front and back waist regions, the elastomeric structure extending completely across the respective waist region and extending beyond lateral sides of the chassis so as to form elastomeric attachment tabs. The elastomeric structure having a predetermined first modulus of elasticity such that when attached to said waist region, a resulting elastomeric waistband portion is defined having an overall second modulus of elasticity that is less than the first modulus of elasticity of the attachment tabs.

29 Claims, 4 Drawing Sheets

U.S. PATENT DOCUMENTS

| | | | |
|---|---|---|---|
| 5,846,232 | A | 12/1998 | Serbiak et al. |
| 6,313,372 | B1 | 11/2001 | Suzuki |
| 6,325,787 | B1 | 12/2001 | Roe et al. |
| 6,336,921 | B1 | 1/2002 | Kato et al. |
| 6,358,350 | B1 | 3/2002 | Glaug et al. |
| 6,432,098 | B1 * | 8/2002 | Kline et al. ............. 604/387 |
| 6,488,202 | B1 | 12/2002 | Seitz et al. |
| 2003/0109842 | A1 | 6/2003 | Louis et al. |
| 2004/0010241 | A1 | 1/2004 | Sanders et al. |

FOREIGN PATENT DOCUMENTS

| | | |
|---|---|---|
| EP | 1350495 A1 * | 10/2003 |
| WO | 9960972 | 12/1999 |
| WO | 9960974 | 12/1999 |
| WO | 0187588 A2 | 11/2001 |
| WO | 03003961 | 1/2003 |

OTHER PUBLICATIONS

U.S. Appl. No. 10/026,122, filed Dec. 17, 2002.

EPO Search Report, Apr. 13, 2004.

* cited by examiner

ABSORBENT ARTICLE WITH UNITARY ELASTOMERIC WAISTBAND WITH MULTIPLE EXTENSION ZONES

TECHNICAL FIELD OF THE INVENTION

The present invention relates generally to the field of absorbent articles and garments, such as children's training pants, disposable diapers, incontinence articles, and the like, and more particularly to an improved waistband configuration for use in such articles.

BACKGROUND

Various types of disposable absorbent articles such as disposable diapers, training pants, swim pants, incontinence articles, and the like, utilize a chassis incorporating an absorbent system and an elastomeric waistband. The waistband provides for enhanced fit, comfort to the wearer, and improved product performance.

Much attention has been paid in the art to development of various elastomeric waistband configurations. For example, U.S. Pat. No. 4,205,679 discloses various embodiments of a pull-on pant-like article having gathered elastic waistband portions. U.S. Pat. No. 4,639,949 describes a disposable absorbent garment having an improved elastic waistband with an elastic element joined in a stretched condition to a marginal portion of an exterior panel of the garment with a plurality of spaced bond points. U.S. Pat. No. 4,904,251 describes a disposable diaper having gathered elasticized front and back waistband portions. Tape fasteners are provided on back side flaps for fastening the front and back regions of the article together on a wearer. U.S. Pat. No. 5,676,661 similarly discloses a diaper configuration having elasticized waistband portions and tape members extending from the side margins of the back waist region. The tape members include a fastening strip, such as a hook-type material, that attaches to a corresponding landing pad material provided on the front waist region to secure the article to a wearer.

With a known commercial disposable diaper (the HUGGIES® brand from Kimberly-Clark Corp. of Neenah, Wis., USA) elasticity is provided to the back waistband by elastomeric strips bonded to side edges of the chassis at the waist region. A non-elastic material strip is bonded to the outboard end of the elastomeric strips, and a micro-hook material strip is laminated to this non-elastic material. For securing the diaper on a wearer, the hook material attaches to a piece of non-woven web material adhered to the outer cover at the front waist region. Thus, with this configuration, the chassis has generally non-elastomeric waistband portions, and the degree of elasticity provided around the waist of a wearer is a function of the elastomeric tab strips.

Conventional elastomeric waistband configurations may, however, be improved upon. For example, with diaper configurations wherein elastomeric waistband portions are defined at the longitudinal ends of the chassis by adhering elastic strands or strips in a tensioned condition to the liner material and/or outer cover, it is very difficult to accurately predict and control the elasticity of the respective portions under multiple wear conditions. As other materials are added or attached at the waistbands, such as containment flaps, the overall elastic modulus of the waistband changes. A change in the outer cover material or liner material will change the elastic modulus of the waistbands, and so forth. To accommodate for such variance, manufactures tend to use more elastic material than would otherwise be necessary. Unfortunately, the elastic materials are relatively expensive.

With the diaper configurations wherein the chassis waistband regions are non-elastomeric and elasticity is provided by elastomeric tab strips, the bonds between the elastomeric strips and chassis sides must be particularly strong to withstand the tensile forces exerted by the strips in use. The same concern applies to the bonds between the elastomeric strips and fastening strips. Many consumers believe that they must stretch the elastic tabs as much as possible in order to obtain a secure fit of the diaper. This results in significant tensile forces being exerted at the bond points. Tab tears at these locations is a common complaint with consumers. Adding additional length to the elastic strips would only add significant cost, may degrade fit and performance, and may impede attachment of both tabs along the front waist region of the chassis. Also, from a manufacturing standpoint, the process of forming the multi-component elastomeric tabs and bonding the tabs to the article chassis is material intensive and relatively complicated.

The present invention provides an improved elastic waistband configuration that may help alleviate deficiencies of current configurations.

SUMMARY

Objects and advantages of the invention will be set forth in part in the following description, or may be obvious from the description, or may be learned through practice of the invention.

In general, the present invention relates to a unique elastomeric waistband configuration for use in a variety of absorbent articles, such as disposable diapers, child's training pants, incontinence articles, diaper pants, disposable swim pants, and the like. For purposes of description only, embodiments of an absorbent article according to the invention will be made with reference herein to a disposable diaper. It should be understood that the invention is not limited to disposable diapers.

An absorbent article according to the invention includes a chassis having a front waist region, a back waist region, and a crotch region extending between the front and back waist regions. An outer cover member and a bodyside liner extend longitudinally between the front and back waist regions. An absorbent body structure is sandwiched between the outer cover member and the bodyside liner. The construction of such a chassis, and suitable materials for the chassis, are well known to those skilled in the art.

An elastomeric structure is attached to at least one of the front and back waist regions. For a disposable diaper embodiment, the elastomeric structure may be attached across the back waist region and extend completely across the respective waist region between lateral sides of chassis. The elastomeric structure may be formed of a single material, such as a strip of elastic material, or as a combination of materials, such as a stretch bonded laminate material. In a disposable diaper embodiment, the elastomeric structure extends completely across the back waist region and beyond the lateral sides of the chassis so as to form elastomeric attachment tabs. The elastomeric structure has a predetermined degree of elasticity, or first modulus of elasticity, such that when attached to the waist region, a resulting elastomeric waistband portion is defined as the combination of the elastomeric structure and the material of the waist region. The elastomeric waistband portion has an overall second modulus of elasticity that is less than the first modulus of elasticity of the elastomeric structure alone (corresponding to that of the attachment tabs).

In a particular embodiment, the elastomeric structure is attached to waistband region of the article in a tensioned state such that upon the elastomeric structure relaxing, the waistband portion is gathered and stretchable at least to an extent permitted by the degree of gathering of the waistband region. The elastomeric structure may be tensioned to a maximum extent prior to attachment to the waist region material, or may be tensioned to an extent less than a maximum elongation such that stretchability of the waistband portion is limited by the degree of gathering of the waist region material and not the elastomeric structure. With this embodiment, the elastomeric attachment tabs are further stretchable upon the waistband portion being stretched to a maximum extent.

In an alternate embodiment, the waistband region of the chassis is extensible and the elastomeric structure is attached to the chassis in a non-extended state with little or no resulting gathering. The maximum elongation will be determined by either the extensibility of the chassis material or the extensibility of the elastomeric structure.

The invention also encompasses embodiments of absorbent articles having an elastomeric waistband portion with varying degrees of elasticity, or a varying modulus of elasticity, along the length of the waistband portion. Such an embodiment may or may not include the elastomeric attachment tabs. The varying modulus of elasticity may be defined with a varying bond pattern between the elastomeric structure and waist region material. For example, the bond pattern may have a defined gradient of bonded surface area that changes along the length of the waistband portion. In one embodiment, there may be a greatest surface area bonding between the elastomeric structure and waist region material along a defined center portion extending on either side of a longitudinal centerline of the chassis. The bonded surface area gradient may then decrease from the centerline portion towards the lateral sides of the chassis. The modulus of elasticity will vary as a function of the bonded surface area gradient.

With a disposable diaper embodiment wherein the elastomeric structure extends laterally outboard of the chassis sides to define elastomeric side tabs, a fastening device may be configured on the elastomeric attachment tabs. The fastening device may be, for example, a releasable adhesive, or a piece of hook material that attaches to a loop or nonwoven material on the outer cover in the front waist region. Various such fastening devices are well known and used in the art for disposable diapers.

Aspects of the invention will be described below in greater detail with reference to embodiments shown in the figures.

DETAILED DESCRIPTION

Figure 1:
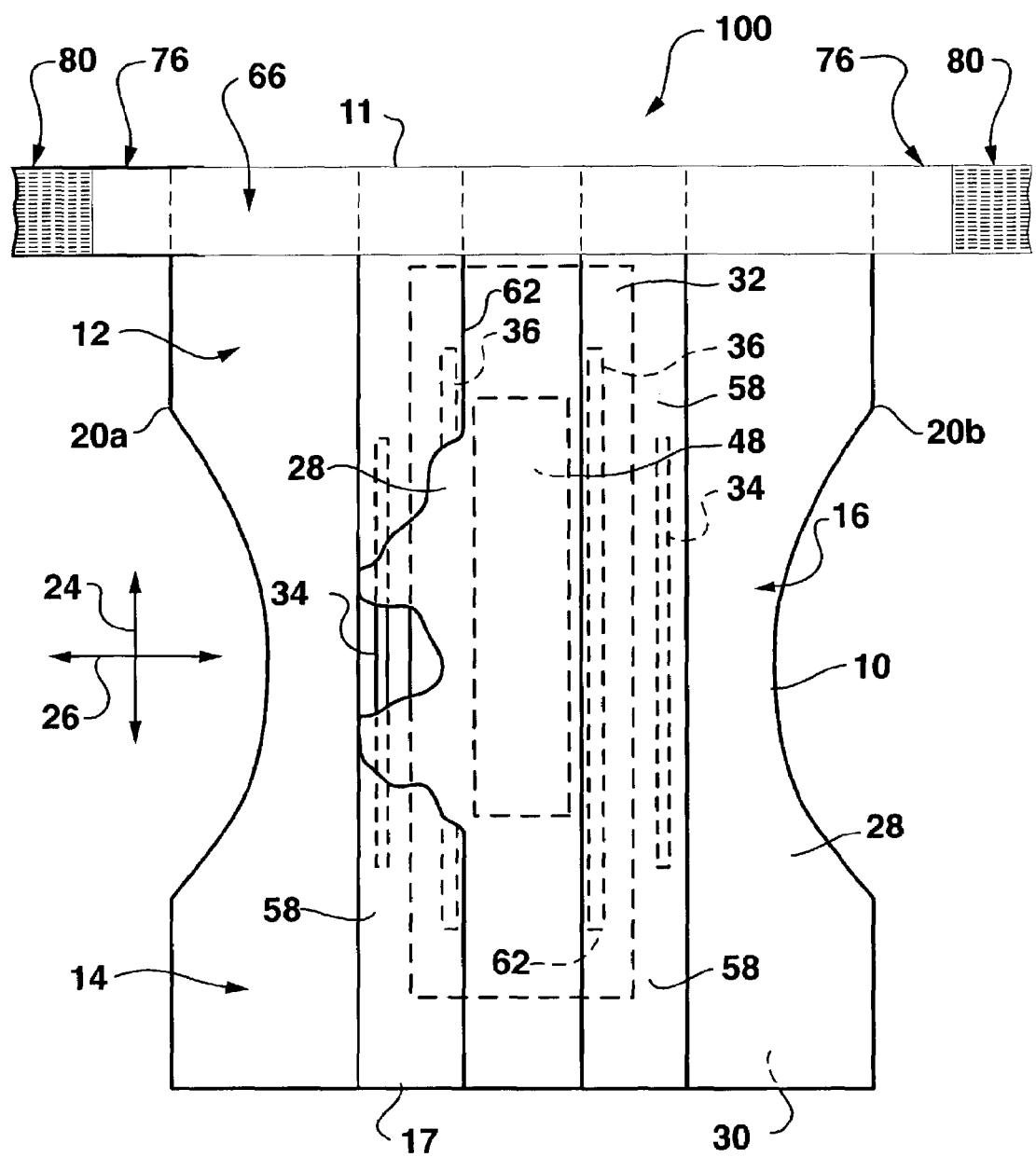
FIG. 1 is a bodyside plan view of an absorbent article according to the invention with all elastic members shown in an extended stretched condition

The invention will now be described in detail with reference to particular embodiments thereof. The embodiments are provided by way of explanation of the invention, and are not meant as a limitation of the invention. For example, features described or illustrated as part of one embodiment may be used with another embodiment to yield still a further embodiment. It is intended that the present invention include these and other modifications and variations as come within the scope and spirit of the invention.

Within the context of the present description, the following terms may have the following meanings:

"Attached" and "joined" refers to the bonding, adhering, connecting, and any other method for attaching or joining two elements. Two elements will be considered to be attached or joined together when they are bonded directly to one another or indirectly to one another, such as when each is directly attached to an intermediate element.

"Extendable" means that property of a material or composite by virtue of which it stretches or extends in the direction of an applied biasing force normally exerted by a consumer by at least about 25% of its relaxed length. An extendable material may or may not have recovery properties. For example, an elastomeric material is an extendable material having recovery properties. A meltblown web may be extendable, but not have recovery properties.

"Elastomeric," "elastic," and "elasticized" refer to a material or composite which can be elongated by at least 25% of its relaxed length and which will recover, upon release of the applied force, at least 10% of its elongation. It is generally preferred that the elastomeric material or composite be capable of being elongated by at least 100%, more preferably by at least 300%, of it relaxed length and recover at least 50% of its elongation. An elastomeric material is an extendable material having recovery properties.

"Neck-bonded" laminate refers to a composite material having an elastic member that is bonded to a non-extensible member while the non-elastomeric member is extended in the machine direction creating a necked material that is elastic in the cross-direction. Examples of neck-bonded laminates are disclosed in U.S. Pat. Nos. 4,965,122; 4,981,747; 5,226,992; and 5,336,545, which are incorporated herein by reference in their entirety for all purposes.

"Reversibly-necked material" refers to a necked material that has been treated while necked to impart memory to the material so that when force is applied to extend the material to it pre-necked dimensions, the necked and treated portions will generally recover to their necked dimensions upon termination of the force. A reversibly-necked material may include more than one layer. For example, multiple layers of spunbonded web, multiple layers of meltblown web, multiple layers of bonded carded web or any other suitable combination of mixtures thereof. The production of reversibly-necked materials is described in U.S. Pat. Nos. 4,965,122 and 4,981,747, incorporated herein by reference for all purposes.

"Stretch-bonded" laminate refers to a composite material having at least two layers in which one layer is a gatherable layer and the other layer is an elastic layer. The layers are joined together when the elastic layer is in an extended condition so that upon relaxing the layers, the gatherable layer is gathered. For example, one elastic member can be bonded to another member while the elastic member is extended at least about 25% of its relaxed length. Such a multilayer composite elastic material may be stretched until the non-extensible layer is fully extended. Examples of stretch-bonded laminates are disclosed, for example, in U.S. Pat. Nos. 4,720,415, 4,789,699, 4781,966, 4,657,802, and 4,655,760, which are incorporated herein by reference in their entirety for all purposes.

"Neck stretch-bonded" laminate" refers a laminate made from the combination of a neck-bonded laminate and a stretch-bonded laminate. Examples of necked stretch bonded laminates are disclosed in U.S. Pat. Nos. 5,114,781 and 5,116,662, which are incorporated herein in their entirety by reference thereto for all purposes. Of particular advantage, a necked stretch bonded laminate can be stretchable in both the machine and cross-machine directions.

"Nonwoven web" refers a web that has a structure of individual fibers or threads which are interlaid, but not in an identifiable, repeating manner. Nonwoven webs may be formed, for example, by a variety of processes including melt-blowing, spunbonding, and bonded carded web processes.

"Sheet" refers to a layer which may be either a film or a nonwoven web.

"Member" when used in the singular can refer to a single element or a plurality of elements.

"Modulus of elasticity" refers to a constant that numerically measures or represents the amount of elasticity a material possesses. Modulus of elasticity may be defined as the slope of a stress strain curve between 0% and 80% of Stretch to Stop of the material as measured by ASTM D2433 "Standard Test Method for Rubber Thread" or a similar test. "Stretch to Stop" of the material is defined as the elongation at which elastic laminate material response to strain is controlled by the non-elastic member of the laminate.

"Tension" refers to a force tending to cause the extension of a body, or to the balancing force within that body resisting the tension. Tension may be expressed in units of grams per unit of width.

Aspects of the invention are explained below by reference to embodiments of a disposable diaper. As mentioned, the invention is not limited to diapers, and as utility for various other absorbent articles, including, training pants, swim pants, incontinence articles, and the like.

FIG. 1 shows a body facing plan view of a representative article 100, in this case a disposable diaper, in its generally flat-out, uncontracted state (i.e., with substantially all elastic induced gathering and contraction removed). The article components are attached or joined together by conventional suitable attachment methods such as adhesive bonds, sonic bonds, thermal bonds, pinning, stitching or any other attachment technique known in the art, as well as combinations thereof. For example, a uniform continuous layer of adhesive, a patterned layer of adhesive, a sprayed pattern of adhesive or an array of separate lines, swirls or spots of construction adhesive may be used to affix the various components.

Figure 2:
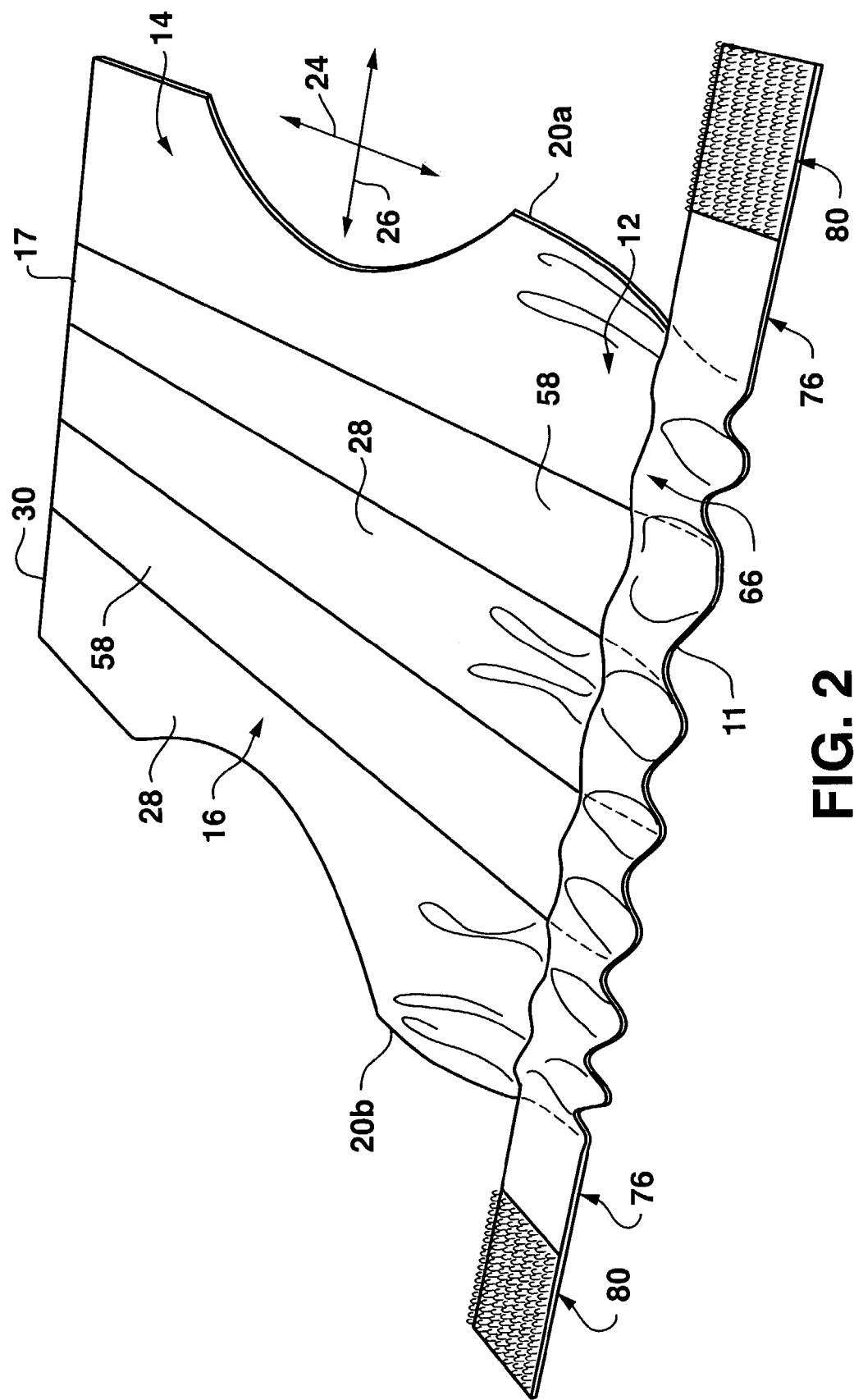
FIG. 2 is a perspective view of an absorbent article according to the invention with the elastic members shown in a relaxed state.

With reference to FIGS. 1 and 2 in general, the representatively shown diaper 100, is illustrated. This diaper 100 is similar in many aspects to the Huggies® brand of disposable diapers from Kimberly-Clark Corporation of Neenah, Wis., USA. The article 100 includes a body or chassis 10 having lateral sides 20a and 20b, a lengthwise, longitudinal direction 24, a lateral, transverse cross-direction 26, a front waist region 14, a back waist region 12, and an intermediate crotch region 16 interconnecting the front and back waist regions. The waist regions 12 and 14 comprise those portions of the article 100 which when worn, wholly or partially cover or encircle the waist or mid-lower torso of the wearer. The front 14 and back 12 waist regions have front and back waistband portions 17, 11. The intermediate crotch region 16 lies between and interconnects the waist regions 14 and 12, and comprises that portion of the article 100 which, when worn, is positioned between the legs of the wearer and covers the lower torso of the wearer. Thus, the intermediate crotch region 16 is an area where repeated fluid surges typically occur in the training pant or other disposable absorbent article.

The diaper 100 will typically include a porous, liquid permeable bodyside liner 28 overlying an absorbent body structure 32, and a substantially liquid impermeable outer cover member 30. The absorbent body structure 32 is positioned and attached between the outer cover member 30 and bodyside liner 28. In certain embodiments, a surge layer 48 may be optionally located adjacent the absorbent structure and attached, for example, by way of an adhesive.

The outer cover member 30 and bodyside liner 28 may be separate sheets joined at the respective lateral sides 20a and 20b. Leg elastics 34 may be incorporated along the lateral side margins of the chassis 10 outboard of the absorbent body structure 32 and are configured to draw and hold the chassis 10 against the legs of the wearer. The elastic members 34 are secured to the chassis 10 in an elastically contracted state so that in a normal under-strain condition, the elastic members 34 effectively contract against the chassis. The use of elastic leg members in absorbent articles such as disposable diapers and training pants is widely known and understood in the art.

Various materials are available and known in the art for use as the outer cover member 30. Constructions of the outer cover member 30 may comprise a woven or non-woven fibrous web layer which has been totally or partially constructed or treated to impart the desired levels of liquid impermeability to selected regions that are adjacent or proximate the absorbent body. Alternatively, a separate liquid impermeable material could be associated with the absorbent body structure 32. The outer cover may include a gas-permeable, nonwoven fabric layer laminated to a polymer film layer which may or may not be gas-permeable. Other examples of fibrous, cloth-like outer cover materials can comprise a stretch thinned or stretch thermal laminate material. Although the outer cover member 30 typically provides the outermost layer of the article, optionally the article may include a separate outer cover component member which is additional to the outer cover member.

The outer cover member 30 may be formed substantially from an elastomeric material. Alternately, the outer cover member may be formed from a non-elastomeric and non-extendable material, or a non-elastomeric and extensible material. The outer cover member 30 may, for example, be composed of a single layer, multiple layers, laminates, spunbond fabrics, films, meltblown fabrics, elastic netting, microporous web, bonded carded webs or foams comprised of elastomeric or polymeric materials. Elastomeric nonwoven laminate webs may include a nonwoven material joined to one or more gatherable nonwoven webs, films, or foams. Stretch bonded laminates (SBL), neck bonded laminates (NBL), and necked stretch bonded Laminates (NSBL) are examples of elastomeric composites. Nonwoven fabrics are any web of material which has been formed without the use of textile weaving processes which produce a structure of individual fibers which are interwoven in an identifiable repeating manner. Examples of suitable materials are spunbond-meltblown fabrics, spunbond-meltblown-spunbond fabrics, spunbond fabrics, or laminates of such fabrics with films, foams, or other nonwoven webs. Elastomeric materials may include cast or blown films or filaments, foams, or meltblown fabrics composed of polyethylene, polypropylene, or polyolefin copolymers, as well as combinations thereof. The outer cover 30 may include materials that have elastomeric or extensible properties obtained through a mechanical process, printing process, heating process, or chemical treatment. For examples such materials may be apertured, creped, neck-stretched, heat activated, embossed, and micro-strained; and may be in the form of films, webs, and laminates.

The bodyside liner 28 may be formed from any one or combination of suitable materials known in the art. Various woven and nonwoven fabrics can be used as the liner 28. For example, the material may include a meltblown web, a spunbonded web, or a bonded-carded-web composed of synthetic continuous or discrete polymer fibers and/or natural fibers, a pattern bonded spunbonded web, airlaid web, or bonded carded web, as well as combinations thereof. The various fabrics can be composed of natural fibers, synthetic fibers or combinations thereof. In particular aspects, the material may be comprised of polymer fibers, networks, laminates, liquid permeable films, cellulosic fibers, rayon, water swellable gels, as well as combinations thereof. Suitable polymers can include polypropylene, polyethylene, polyester, and bicomponent materials composed of these polyolefins. The liner may be elastomeric or extensible or both.

The liner 28 may be composed of a substantially hydrophobic material, and the hydrophobic material may optionally be treated with a surfactant or otherwise processed to impart a desired level of wettability and hydrophilicity. In a particular embodiment of the invention, the material can be a nonwoven, spunbond polypropylene fabric. The fabric can be surface treated with an operative amount of surfactant, such as about 0.6% AHCOVEL Base N62 surfactant, available from ICI Americas, a business having offices located in Wilmington, Del. The surfactant can be applied by any conventional means, such as spraying, dipping, printing, brush coating or the like. The fibers forming the nonwoven material may be mono-component, bi-component, or multi-component fibers, and combinations thereof.

The liner 28 may include blends or laminates of fibers, scrim, webs, and films with perforations, apertures, creping, heat activation, embossing, micro-straining, chemical treatment, or the like, as well as combinations thereof.

The article 100 may incorporate separate containment flaps 58 attached to the chassis 10 at the waistband portions 11, 17 and along a longitudinal side thereof outboard of the absorbent structure 32. The flaps 58 may contain elastic members 36 along at least a portion of their free laterally inward side 62. The construction of such containment flaps 58 is well known and need not be described in detail. Suitable constructions and arrangements for the containment flaps 58 are described, for example, in U.S. Pat. No. 4,704,116, which is incorporated herein by reference for all purposes.

The absorbent body structure 32 can be any structure or combination of components which are generally compressible, conformable, non-irritating to a wearer's skin, and capable of absorbing and retaining liquids and certain body wastes. The structure 32 may be extensible or elastomeric. For example, the structure 32 may include an absorbent web material of cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic materials, pigments, lotions, odor control agents or the like, as well as combinations thereof. In a particular embodiment, the absorbent web material is a matrix of cellulosic fluff and superabsorbent hydrogel-forming particles. The cellulosic fluff may comprise a blend of wood pulp fluff. One preferred type of fluff is identified with the trade designation CR 1654, available from U.S. Alliance of Childersburg, Ala., USA, and is a bleached, highly absorbent wood pulp containing primarily soft wood fibers. The absorbent materials may be formed into a web structure by employing various conventional methods and techniques. For example, the absorbent web may be formed with a dry-forming technique, an air forming technique, a wet-forming technique, a foam-forming technique, or the like, as well as combinations thereof. Methods and apparatus for carrying out such techniques are well known in the art.

As a general rule, the superabsorbent material is present in the absorbent web in an amount of from about 0 to about 90 weight percent based on total weight of the web. The web may have a density within the range of about 0.10 to about 0.35 grams per cubic centimeter.

Superabsorbent materials are well known in the art and can be selected from natural, synthetic, and modified natural polymers and materials. The superabsorbent materials can be inorganic materials, such as silica gels, or organic compounds, such as crosslinked polymers. Typically, a superabsorbent material is capable of absorbing at least about 15 times its weight in liquid, and desirably is capable of absorbing more than about 25 times its weight in liquid. Suitable superabsorbent materials are readily available from various suppliers. For example, Favor 880 superabsorbent is available from Stockhausen GmbH of Germany; and Drytech 2035 is available from Dow Chemical Company, of Midland Mich., USA.

After being formed or cut into a desired shape, the absorbent web material may be wrapped or encompassed by a suitable wrap that aids in maintaining the integrity and shape of the absorbent structure 32.

The absorbent web material may also be a coform material. The term "coform material" generally refers to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic absorbent materials, treated polymeric staple fibers and the like. Any of a variety of synthetic polymers may be utilized as the melt-spun component of the coform material. For instance, in some embodiments, thermoplastic polymers can be utilized. Some examples of suitable thermoplastics that can be utilized include polyolefins, such as polyethylene, polypropylene, polybutylene and the like; polyamides; and polyesters. In one embodiment, the thermoplastic polymer is polypropylene. Some examples of such coform materials are disclosed in U.S. Pat. No. 4,100,324 to Anderson, et al.; U.S. Pat. No. 5,284,703 to Everhart, et al.; and U.S. Pat. No. 5,350,624 to Georger, et al.; which are incorporated herein in their entirety by reference thereto for all purposes.

The absorbent body structure 32 may include an elastomeric coform absorbent web material, for example as described in U.S. Pat. Nos. 4,663,220 and 4,741,949. In particular aspects, the elastomeric coform material can have an overall coform basis weight which is at least a minimum of about 50 $g/m^2$. The coform basis weight can alternatively be at least about 100 $g/m^2$ and can optionally be at least about 200 $g/m^2$ to provide improved performance. In addition, the coform basis weight can be not more than about 1200 $g/m^2$. Alternatively, the coform basis weight can be not more than about 900 $g/m^2$, and optionally, can be not more than about 800 $g/m^2$ to provide improved benefits. These values are important because they can provide the absorbent body structure with desired stretchability and structural stability without excessively degrading the physical properties or the liquid-management functionalities of the absorbent body structure. Retention portions having excessively low proportions of elastomeric coform material may not be sufficiently stretchable. An absorbent web material having excessively large amounts of elastomeric coform materials can exhibit an excessive degradation of their absorbency functionalities, such as an excessive degradation of intake, distribution and/or retention properties.

Other examples of elastomeric absorbent structures are described in U.S. Pat. No. 6,362,389 B1, incorporated herein by reference for all purposes.

The absorbent web material utilized in the absorbent body structure 32 is also selected so that the individual absorbent body structure possesses a particular individual total absorbency depending on the intended article of use. For example, for infant care products, the total absorbency can be within the range of about 200-900 grams of 0.9 wt % saline, and can typically be about 500 g of saline. For adult care products, the total absorbency can be within the range of about 400-2000 grams of saline, and can typically be about 1300 g of saline. For feminine care products, the total absorbency can be within the range of about 7-50 grams of menstrual fluid, and can typically be within the range of about 30-40 g of menstrual fluid.

As described, the absorbent body structure 32 may also include a surge management layer 48 which helps to decelerate and diffuse surges or gushes of liquid that may be rapidly introduced into the absorbent body of the article. Desirably, the surge management layer can rapidly accept and temporarily hold the liquid prior to releasing the liquid into the storage or retention portions of the absorbent structure. The surge layer can be located below the bodyside liner layer 28. Alternatively, the surge layer may be located on the body facing surface of the bodyside liner 28. Examples of suitable surge management layers are described in U.S. Pat. Nos. 5,486,166; and 5,490,846. Other suitable surge management materials are described in U.S. Pat. No. 5,820,973. The entire disclosures of these patents are hereby incorporated by reference in their entirety for all purposes.

Referring to the figures in general, an absorbent article 100 according to the invention includes an elastomeric structure 66 attached to at least one of the front and back waist regions 11, 17. In the disposable diaper embodiment illustrated in FIG. 1, the elastomeric structure 66 is attached only to the back waist region 12. It should be appreciated, however, that an article having an elastomeric structure 66 attached at the front and back waist regions is within the scope and spirit of the invention.

It has been found that a unitary elastomeric structure 66 attached completely across the transverse width of the chassis 10 at a waist region simplifies the manufacturing and assembly process of the article 100, and enables more precise prediction and control of the performance of an elastomeric waistband. The elastomeric structure 66 may be formed of any number of suitable elastomeric materials, as described below, and will have a generally known degree of elasticity, or first modulus of elasticity. Elastomeric waistbands are typically designed to ensure a comfortable and secure fit of the product under normal use conditions. Waistbands with an excessively high tension of the elastic elements result in an uncomfortable fit, red-marking, and/or difficulty in pulling a pant-like structure up or down. On the other hand, a waistband portion with too low of a tension results in a substantial loss of elasticity of the waistband portion for repeated cycles of the article, or as the elastomeric materials experience stress relaxation in use. This concern is also relevant with training pant articles wherein the user typically pulls the article down and back up to go to the bathroom, etc. The loss of elasticity is also an issue with disposable diapers wherein the diaper may be removed to check whether it has been soiled or wetted. To compensate for potential loss of elasticity under normal use conditions, manufacturers typically incorporate waist elastics with a relatively high tension. However, as discussed, this may lead to product comfort issues. This is particularly true if the elastomeric portions of the waistband do not span the entire circumference of the waist opening of the article, but are provided in discrete transversely extending sections or portions across the waist opening. With this type of arrangement, the tension forces are not distributed evenly across the waistband and may negatively affect the fit or the article.

In accordance with the present invention, a unitary elastomeric structure 66 having a known modulus of elasticity for a given tensile stretching force is attached completely across the waist region of the article 100 between the lateral sides 20a and 20b. This results in an elastomeric waistband portion extending completely between the lateral sides 20a and 20b having an overall modulus of elasticity that is a function of the combination of the elastomeric structure 66 and materials of the waist region to which it is attached. By varying the attachment or bond points between the elastomeric structure 66 and waist region materials (for example by bond length, spacing, etc.), the overall modulus of elasticity of the elastomeric waistband portion can be varied across the article 100 between the lateral sides 20a and 20b. In other words, by increasing or decreasing the joined or bonded surface area between the elastomeric structure 66 and waist region 12, the overall elasticity and modulus of the waistband portion can be adjusted. The modulus for the composite can also be altered by the shape of the waist and attachment areas, attachment of the elastomeric structure to non-extensible chassis pieces, and intentional non-attachment of the elastomeric structure to non-extensible chassis areas.

Referring to the figures in general, the elastomeric structure 66 is illustrated as a band 68 of a suitable elastomeric material. Suitable elastomeric materials can include, for example, elastic strands, Lycrae® elastics, elastic films, nonwoven elastic webs, meltblown or spunbond elastomeric fibrous webs, as well as combinations thereof. Examples of elastomeric materials include ESTANE® elastomeric polyurethanes (available from BF Goodrich & Co. located in Cleveland, Ohio), PEBAX® elastomers (available from AtoChem located in Philadelphia, Pa.), HYTREL® elastomeric polyester (available from El Dupont de Nemours located in Wilmington, Del.), KRATON® elastomer (available from Shell Chemical Company located in Houston, Tex.), or the like, as well as combinations thereof. A suitable elastomeric material for the elastomeric structure 66 may comprise a stretch-thermal laminate (STL), a neck-bonded laminate (NBL), a reversibly-necked laminate, or a stretch-bonded laminate (SBL) material. Methods of making such materials are described, for example, in U.S. Pat. Nos. 4,663,220; 5,226,992; and the EP Application No. 0 217 032, all of which are incorporated herein by reference in their entirety for all purposes.

In the illustrated embodiment, the elastomeric structure 66 is defined by a band 68 of the elastomeric material attached to the waist region 12 with a defined bond pattern 70. As particularly illustrated in the perspective view of FIG. 2, the elastomeric material may be attached to the chassis material between the lateral sides 20a and 20b in a tensioned state, such that upon releasing the elastic band, the waist region material is gathered resulting in a stretchable or extendable waistband region. The waistband region is stretchable at least to an extent permitted by the degree of gathering of the waistband region, as is commonly understood in the art. In one embodiment, the elastomeric band 68 may be attached in a tensioned state that is less than its maximum elongation such that stretchability of the waistband portion is limited by the degree of gathering of the waistband materials, and not the elastomeric band 68.

Figure 3:
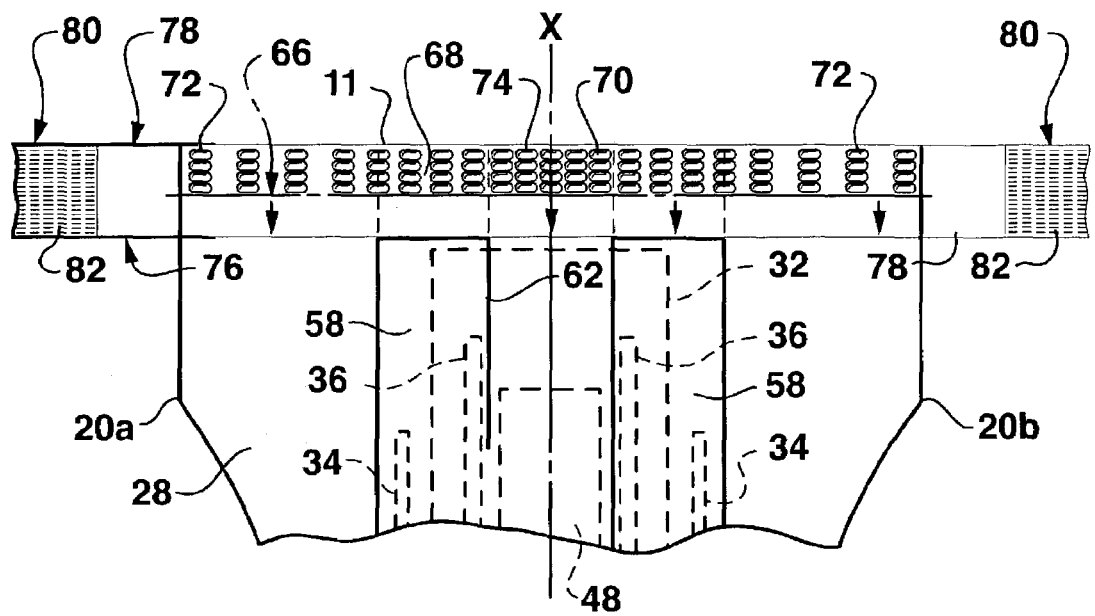
FIG. 3 is a partial bodyside plan view of a waistband portion incorporating an elastomeric structure according to the invention.
Figure 4:
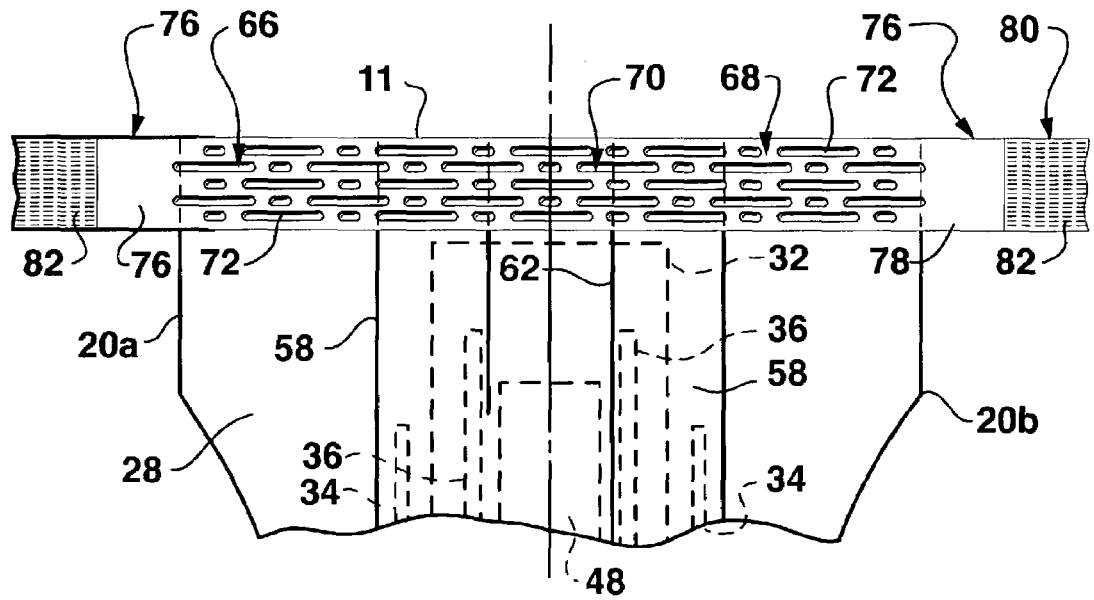
FIG. 4 is a partial bodyside plan view of an alternate embodiment of a waistband portion according to the invention.
Figure 5:
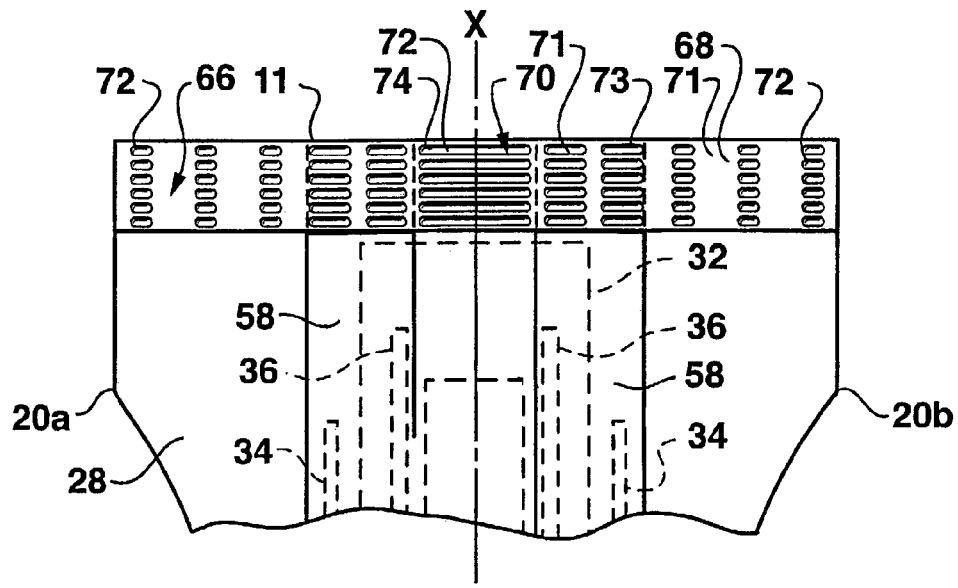
FIG. 5 is a partial bodyside plan view of still another embodiment of a waistband portion according to the invention.

Referring to FIGS. 3 through 5, it can be seen that the bond pattern 70 may vary across the width of the waistband portion between the lateral sides 20a and 20b. For example, referring to FIG. 3, the density of the bond points (number of bond points/surface area) is greatest at a center portion 74 extending on each side of a longitudinal centerline X of the chassis 10. Thus, along this center portion 74, there is a given modulus of elasticity that is a function of the bonded surface area between the elastomeric band 68 and waist region materials. In the waistband regions laterally outboard of the center portion 74, the density of bond points decreases and, thus, the modulus of elasticity is varied in these regions (assuming extensible waist region materials). The density of the bond points may decrease according to an established gradient towards the direction of the respective lateral sides 20a and 20b. Referring to FIG. 3, for example, the gradient may reflect a linear change in the density of bond points, and thus result in a linear change in the modulus of elasticity from the centerline X towards each of the lateral sides 20a and 20b. This particular arrangement may be beneficial in that the waistband region will be more elastic towards the sides of the wearer as compared to the centerline or small of the back region where, under normal use conditions, waistband elasticity at this region is not critical. On the other hand a reverse gradient of bond points may provide increased protection against waist leakage. Thus, the varying bond pattern allows for varying degrees of elasticity across the waistband region with a simple unitary elastomeric structure.

FIG. 5 illustrates an alternative embodiment of a varying gradient of bond points 72 resulting in a varying modulus of elasticity across the waistband region. In this embodiment, the bottom points 72 are defined by elongated generally linear bonds wherein the length of each point 72 is varied to vary the bonded surface area. For example, in the center region 74, the bond points 72 are generally continuous. In an immediately outboard section 73, the bond points 72 are defined by shorter linear bonds with a greater spacing therebetween. Similarly, in the most outboard sections 71, the bonds 72 are defined by even shorter linear bonds.

It should be appreciated that virtually any configuration of bond shapes or patterns may be used to define a varying bond gradient across the waistband region between the lateral sides 20a and 20b of the article 100.

The invention also incorporates articles 100 wherein the elastomeric structure is bonded to the waist region 11 of the article with a generally uniform bond pattern between the lateral sides 20a and 20b. Such a bond pattern is illustrated, for example, in FIG. 4. It should be appreciated that virtually any combination of bond shapes and patterns may be utilized in this regard. With this embodiment, the elastomeric structure 66 extends laterally outboard of the sides 20a and 20b of the chassis 10 and defines attachment tabs 76, as can be particularly seen in FIGS. 1 through 4. Referring to FIG. 3, the attachment tabs 76 defined by the elastomeric structure 66 may also be utilized with an embodiment having a varying bond pattern across the waistband region. The attachment tabs 76 are thus defined by a transversely extending portion of the elastomeric band 68. This portion 78 has the elasticity of the original elastomeric structure 66 before attachment to the waist region material. Thus, this portion 78 has a different modulus of elasticity as compared to the elastomeric waist band region extending between the lateral sides 20a and 20b. Additionally, the attachment of the elastic structure 66 to the hook material 82 results in another composite modulus. Upon use of the article 100, the elastomeric portions 78 will have different elastic characteristics as compared to the remaining elastomeric waist band region.

The attachment tabs 76 may incorporate any manner of conventional fastening device 80 for securing the article 100 to a wearer. For example, in the illustrated embodiment, the fastening device 80 is defined by conventional micro-hook material 82 that attaches to a nonwoven material (not shown) provided on the outside of the front region, as is commonly understood in the art. The fastening device 80 may also be a releasable adhesive, mechanical fastener, and so forth.

The configuration of embodiments 1 through 4 may be beneficial in the situation wherein upon securing the article 100 to a wearer, consumers tend to stretch the elastomeric portions 78 of the tabs 76 to a perceived maximum extent. Even if this is done, the waistband regions between the lateral sides 20a and 20b will still have some degree of stretchability and thus tension across the waistband region is controlled.

In an alternate embodiment, the elastomeric band 68 may be attached to the waist region of the article 10 with the elastomeric band 68 in a less than fully tensioned state, for example, at about 50 percent or less of its maximum elongation. With this configuration, the tabs will initially stretch out and then the waist region will also stretch upon a threshold stretching force being applied. On the other hand, extension of the waist region before the tabs may be achieved by through shape changes of the elastomeric structure. For example, the elastomeric structure may be significantly narrower in the waist region as compared to the tabs 76.

Figure 6:
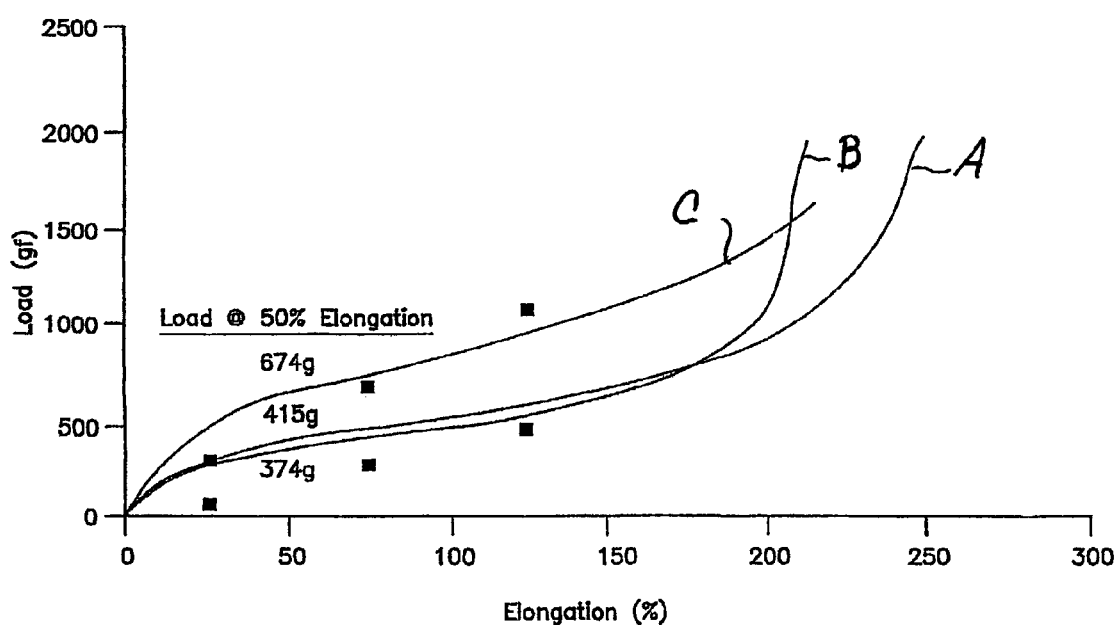
FIG. 6 is a graph of stress/strain curves for three elastomeric materials.

FIG. 6 is a graph of the stress/strain curves for three different types of elastomeric materials, and is provided to conceptually illustrate differences in the elastic modulus between various elastomeric materials. Each of the materials is representative of an elastomeric material that may be used to form portions of the waistbands in articles according to the invention. Material "A" was a laminate based LYCRA®) spandex. Material "B" was a filament based laminate made up of 80% KRATON® G1730, 13% tackifier, and 7% wax. Material "C" was a film including 65.5.% KRATON® G1730, a low molecular weight polyethylene wax, and a pressure sensitive adhesive. Filaments of 80% KRATON®, 13% tackifier, and 7% wax were overlaid on the film.

The elastic modulus of a material relates to the stress relaxation (load loss) and stress-elongation of the material. Stress relaxation of an elastomeric material is defined as the force required to hold a given elongation constant over a period of time. A percentage of load loss may be calculated from knowledge of initial and final loads over the time period, and may be acquired over a given time period using the Testworks data acquisition capability of an MTS Sintech tester. The stress-elongation behavior of the material is a measure of the tension necessary to elongate the material a given percentage. Referring to FIG. 6, the various loads (tension) are recorded for 50% elongation of the respective materials. Samples of the materials may be tested using a Sintech 1/S testing frame. Rectangular laminate samples having a 3-inch width are clamped at a grip-to-grip distance of 3 inches and pulled at a cross-head displacement of 20 inches/minute. The samples were tested to about 2000 grams load limit. The elongation was calculated from knowledge of the change in length and the original length of the sample. The tension at 50% elongation was calculated from the acquired data.

The amount of tension a material delivers to the body after a period of time may be determined by crossing the stress-relaxation data with the stress-elongation curve. For example, material C may have a stress-relaxation of 50% over a 12 hour period. If the material is initially stretched to 50% elongation (load of 674 grams), then at 12 hours the material will deliver about one-half of its initial tension (about 337 grams)

For testing purposes, reference may also be made to ASTM Test Method D2433 "Standard Test Methods for Rubber Thread." Sections 20-22 of the ASTM standard may be referred to for tensile strength testing; sections 23-24 for elongation at break; section 25 for stress at a predetermined elongation; and sections 35-39 for stress relaxation (load loss).

It should be understood that resort may be had to various other embodiments, modifications, and equivalents to the embodiments of the invention described herein which, after reading the description of the invention herein, may suggest themselves to those skilled in the art without departing from the scope and spirit of the present invention.

What is claimed is:

1. An absorbent article, comprising:
a chassis having a front waist region, a back waist region, and a crotch region extending between said front and back waist regions;
an outer cover member and a bodyside liner extending longitudinally between said front and back waist regions;
an absorbent body structure sandwiched between said outer cover member and said bodyside liner;
a unitary elastomeric structure attached to at least one of said front waist region or said back waist region, said elastomeric structure extending completely across said respective waist region and extending beyond lateral sides of said chassis so as to form elastomeric attachment tabs,
said elastomeric structure having a predetermined first modulus of elasticity such that when attached to said waist region, a resulting elastomeric waistband portion is defined having an overall second modulus of elasticity that is less than said first modulus of elasticity of said attachment tabs.

2. The absorbent article as in claim 1, wherein said article is a disposable diaper.

3. The absorbent article as in claim 1, wherein said elastomeric structure comprises a band of elastomeric material.

4. The absorbent article as in claim 1, wherein said elastomeric structure is attached to said waistband region in a tensioned state such that said resulting elastomeric waistband portion is gathered and stretchable at least to an extent permitted by the degree of gathering of said waistband region.

5. The absorbent article in claim 4, wherein said elastomeric structure is tensioned to an extent less than a maximum elongation of said elastomeric structure such that stretchability of said waistband portion is limited by said degree of gathering, and said elastomeric attachment tabs are further stretchable upon said waistband portion being stretched to a maximum.

6. The absorbent article as in claim 1, wherein said waistband region is extensible, said elastomeric structure being attached to said waistband region in an untensioned state.

7. The absorbent article as in claim 1, wherein said elastomeric waistband portion comprises a varying modulus of elasticity therealong.

8. The absorbent article as in claim 7, wherein said elastomeric waistband portion comprises an increasing modulus of elasticity from a chassis centerline thereof towards said lateral sides.

9. The absorbent article as in claim 7, wherein said elastomeric waistband portion comprises a decreasing modulus of elasticity from a chassis centerline thereof towards said lateral sides.

10. The absorbent article as in claim 7, wherein said elastomeric structure is bonded to said waist region with a varying bond pattern to achieve said varying modulus of elasticity across said elastomeric waistband portion.

11. The absorbent article as in claim 8, wherein said elastomeric structure is bonded to said waist region with a greatest surface area bond coverage along a defined center portion extending laterally across said centerline, and is bonded to said waist region with less surface area bond coverage between said defined center portion and said lateral sides.

12. The absorbent article as in claim 11, wherein said less surface area bond coverage decreases according to a defined gradient.

13. The absorbent article as in claim 12, wherein said gradient is linear.

14. The absorbent article as in claim 1, further comprising a fastening device configured on said elastomeric attachment tabs.

15. The absorbent article as in claim 14, wherein said fastening device comprises an adhesive.

16. The absorbent article as in claim 14, wherein said fastening device comprises a hook material, said hook material engageable with a nonwoven web material on an outer side of said front waist region.

17. The absorbent article as in claim 1, wherein said absorbent structure comprises a band of stretch bonded laminate material.

18. An absorbent article, comprising:
a chassis having a front waist region, a back waist region, and a crotch region extending between said front and back waist regions;
an outer cover member and a bodyside liner extending longitudinally between said front and back waist regions;
an absorbent body structure sandwiched between said outer cover member and said bodyside liner;
a unitary elastomeric structure attached to at least one of said front waist region or said back waist region, said elastomeric structure extending completely across said respective waist region and extending beyond lateral sides of said chassis so as to form elastomeric attachment tabs; and
wherein said elastomeric structure is bonded to said waist region with a varying bond pattern resulting in a varying modulus of elasticity across said elastomeric waistband portion.

19. The absorbent article as in claim 18, wherein said elastomeric structure is bonded to said waist region with a greatest surface area bond coverage along a defined center portion extending laterally across a longitudinal centerline of said chassis, and is bonded to said waist region with less surface area bond coverage between said defined center portion and said lateral sides.

20. The absorbent article as in claim 19, wherein said less surface area bond coverage decreases according to a defined gradient.

21. The absorbent article as in claim 20, wherein said gradient is linear.

22. The absorbent article as in claim 18, wherein said elastomeric structure extends beyond said lateral sides of said chassis and defines elastomeric attachment tabs, said attachment tabs having a modulus of elasticity different from said varying modulus of elasticity of said waistband portion.

23. The absorbent article as in claim 22, further comprising a fastening device configured on said elastomeric attachment tabs.

24. A disposable absorbent diaper, comprising:
   a chassis having a front waist region, a back waist region, and a crotch region extending between said front and back waist regions;
   an outer cover member and a bodyside liner extending longitudinally between said front and back waist regions;
   an absorbent body structure sandwiched between said outer cover member and said bodyside liner;
   an elastomeric structure attached to said back waist region, said elastomeric structure extending completely across said back waist region and extending beyond lateral sides of said chassis so as to form elastomeric attachment tabs,
   said elastomeric structure attached in a tensioned state to at least one material along a transverse portion of said waist region so as to define an elastomeric waistband portion having a modulus of elasticity that is less than a modulus of elasticity of said attachment tabs.

25. The diaper as in claim 24, wherein said elastomeric structure comprises a unitary band of elastomeric material.

26. The diaper as in claim 24, wherein said elastomeric waistband portion comprises an increasing modulus of elasticity from a chassis longitudinal centerline towards said lateral sides.

27. The diaper as in claim 26, wherein said elastomeric structure is bonded to said waist region with a varying bond pattern to achieve said varying modulus of elasticity across said elastomeric waistband portion.

28. The diaper as in claim 25, wherein said elastomeric structure is bonded to said outer cover member and said bodyside liner along said elastomeric waistband portion.

29. The diaper as in claim 28, further comprising containment flaps disposed longitudinally along said bodyside liner on opposite sides of said absorbent structure, said containment flaps extending to said back waist region, said elastomeric structure bonded to said containment flaps.

* * * * *